(12) United States Patent
Seaman et al.

(10) Patent No.: US 10,981,131 B2
(45) Date of Patent: Apr. 20, 2021

(54) MICROPARTICLE PRODUCTION PROCESS AND APPARATUS

(71) Applicant: MIDATECH PHARMA (WALES) LIMITED, Cardiff South Glamorgan (GB)

(72) Inventors: Paul Seaman, Cardiff (GB); Huw Jones, Cardiff (GB); Liam McAleer, Cardiff (GB)

(73) Assignee: MIDATECH PHARMA (WALES) LIMITED, South Glamorgan (GB)

( * ) Notice: Subject to any disclaimer, the term of this patent is extended or adjusted under 35 U.S.C. 154(b) by 169 days.

(21) Appl. No.: 15/780,211

(22) PCT Filed: Dec. 16, 2016

(86) PCT No.: PCT/EP2016/081436
§ 371 (c)(1),
(2) Date: May 30, 2018

(87) PCT Pub. No.: WO2017/103113
PCT Pub. Date: Jun. 22, 2017

(65) Prior Publication Data
US 2019/0193037 A1 Jun. 27, 2019

(30) Foreign Application Priority Data
Dec. 18, 2015 (GB) ..................... 1522423

(51) Int. Cl.
*B01J 2/08* (2006.01)
*B01J 2/04* (2006.01)
*B01J 2/18* (2006.01)

(52) U.S. Cl.
CPC . *B01J 2/08* (2013.01); *B01J 2/04* (2013.01); *B01J 2/18* (2013.01)

(58) Field of Classification Search
CPC ..................... B01J 2/08; B01J 2/04
See application file for complete search history.

(56) References Cited

U.S. PATENT DOCUMENTS

| 4,663,093 A | 5/1987 | Haas |
| 6,998,074 B1 * | 2/2006 | Radulescu ........... A61K 9/1682 |
| | | 264/14 |

(Continued)

FOREIGN PATENT DOCUMENTS

| DE | 19750679 | 5/1999 |
| EP | 2305372 | 4/2011 |

(Continued)

*Primary Examiner* — Nathan T Leong
(74) *Attorney, Agent, or Firm* — Rudy J. Ng; Carol L. Francis; Bozicevic, Field & Francis LLP

(57) ABSTRACT

Provided is an apparatus for producing solid polymeric microparticles, the apparatus comprising a plurality of liquid droplet generators for forming liquid droplets of a first liquid, and a nozzle for forming a jet of a second liquid, wherein the plurality of liquid droplet generators and the nozzle are arranged relative to each other such that, in use, liquid droplets from the plurality of liquid droplet generators pass through a gas into said jet of second liquid. Also provided is a process for producing solid microparticles, the process comprising: providing a first liquid comprising a solute and a solvent, the solute comprising a biocompatible polymer, the concentration of polymer in the first liquid being at least 10% w/v, 'w' being the weight of the polymer and 'v' being the volume of the solvent, providing a plurality of liquid droplet generators operable to generate liquid droplets, providing a jet of a second liquid, causing the plurality of liquid droplet generators to form liquid droplets of the first liquid, passing the liquid droplets through a gas to contact the jet of the second liquid so as to cause the solvent to exit the droplets, thus forming solid microparticles, the solubility of the solvent in the second liquid being (Continued)

at least 5 g of solvent per 100 ml of second liquid, the solvent being substantially miscible with the second liquid.

20 Claims, 3 Drawing Sheets

(56) References Cited

U.S. PATENT DOCUMENTS

| | | | |
|---|---|---|---|
| 8,313,676 | B2 | 11/2012 | Bohmer et al. |
| 2011/0185631 | A1 | 8/2011 | Subramanian |
| 2013/0259961 | A1* | 10/2013 | Palmer .................. B01J 2/18 425/10 |
| 2014/0242514 | A1 | 8/2014 | Inoue et al. |

FOREIGN PATENT DOCUMENTS

| | | |
|---|---|---|
| GB | 2398241 | 8/2004 |
| GB | 2512309 | 10/2014 |
| JP | 2011020055 A | 2/2011 |
| WO | 1995/013176 | 5/1995 |
| WO | 1995013176 | 5/1995 |
| WO | 2012/042273 | 4/2012 |
| WO | 2012/042274 | 4/2012 |
| WO | 2013/014466 | 1/2013 |
| WO | 2016/075211 | 5/2016 |

* cited by examiner

Schematic diagram of printhead

MICROPARTICLE PRODUCTION PROCESS AND APPARATUS

FIELD OF THE INVENTION

The present invention relates to an apparatus and method for making polymeric microparticles, including microparticles that encapsulate a pharmaceutical payload.

BACKGROUND TO THE INVENTION

Methods and related apparatus for the production of polymeric microspheres are known. In particular processes, the formation of solidified microspheres is achieved by bringing two fluids together within tightly-controlled parameters, inducing a process of desolvation. Fluid 1, known as the 'dispersed phase', comprises a biocompatible polymer dissolved in one or more solvents. This combination forms a solution into which a payload, such as an active pharmaceutical ingredient (API), can then be dissolved. Droplets of the dispersed phased are ejected into a second fluid, known as 'the continuous phase'. Contact between these begins a process whereby the solvent is extracted from the polymer and payload, yielding precipitated payload-carrying polymer microspheres within what can then be considered a waste fluid. In certain processes the droplet ejection process makes use of the piezoelectric effect, whereby a piezo crystal undergoes distortion when an electric pulse is applied. This distortion results in a pressure pulse, forcing a droplet to be ejected from a nozzle and also creating negative pressure to pull in more fluid once the droplet has been ejected. Many off-the-shelf devices make use of this principle to generate droplets, particularly within the printing industry.

U.S. Pat. No. 6,998,074 describes a method for forming polymer microspheres in which polymeric material is dispensed from an orifice of an ink-jet printhead while the orifice is immersed in a liquid.

WO95/13176 describes a process and device for producing plastic particles from droplets of plastic.

WO2012/042273 and WO2012/042274 describe apparatus and process for the preparation of solid beads that encapsulate a bioactive agents and which are suitable for use in sustained release, e.g., via depot injection.

WO2013/014466 describes a bead collection device and method for separating beads from a carrier fluid.

There remains an unmet need for a microparticle production process and related apparatus that offer increased throughput and/or efficiency compared with the prior described methods of production. The ability to produce large quantities of microparticles of uniform properties in a controlled manner, whilst minimising waste materials, would be desirable, e.g., for pharmaceutical industrial scale-up. The present invention seeks to address these and other needs.

BRIEF DESCRIPTION OF THE INVENTION

Broadly, the present invention relates to an apparatus and method for producing polymeric microparticles in which a plurality (e.g. an array) of droplet generators are configured to dispense liquid droplets into a common stream of a second liquid (the continuous phase). The present inventors have surprisingly found that the stream of second liquid need not be in contact with a conduit or flow channel, but may take the form of a jet (i.e. a coherent stream of fluid projected into a surrounding medium from a nozzle). Moreover, the droplets may be dispensed in parallel, spaced along the direction of flow of the stream of second liquid. Prior described methods envisage a 1:1 relationship between droplet generator and flow channel. However, through experimentation, the present inventors have found that precipitation of the droplets upon coming into contact with the second liquid is virtually instant and that dispensing droplets directly along the line of flow of the stream of second liquid (e.g. having a droplet generator nozzle plate aligned with the line of flow of a jet of second liquid) achieves formation of microparticles without undue coalescence and leads to a significant reduction in the consumption of the second liquid (continuous phase), which in turn reduces cost and waste from the process.

Accordingly, in a first aspect the present invention provides an apparatus for producing solid polymeric microparticles, the apparatus comprising:

a plurality of liquid droplet generators for forming liquid droplets of a first liquid; and a nozzle for forming a jet of a second liquid, wherein the plurality of liquid droplet generators and the nozzle are arranged relative to each other such that, in use, liquid droplets from the plurality of liquid droplet generators pass through a gas into said jet of second liquid.

In some cases, the plurality of liquid droplet generators comprise at least one piezoelectric component operable to generate droplets. In particular, the droplet generators may operate in drop-on-demand mode. The apparatus may further comprise a signal generator operable to supply an electric field to the piezoelectric component.

In some cases, the plurality of liquid droplet generators are in the form of an inkjet printhead.

In some cases the plurality of liquid droplet generators each comprise a droplet generator outlets and wherein the droplet generator outlets are in a line or an array. In particular, the line or array of droplet generator outlets may be substantially parallel to the jet direction of said nozzle. In this context, substantially parallel is taken to mean an offset of not more than 30° from parallel, optionally not more than 5° from parallel. The angle of offset may be determined, for example, by viewing the apparatus from above ("bird's eye view") and considering the line of the jet direction from the nozzle and the line formed by the droplet generator outlets and notionally extending these lines to their point of intersection. In some cases the jet direction from the nozzle will be in line with the line formed by the droplet generator outlets, when viewed from above (an example of this arrangement is depicted in FIG. 3).

In some cases, the number of liquid droplet generator outlets is in the range 5 to 2500, optionally 256, 512 or 1024. In particular, the number of liquid droplet generator outlets may be in the range 100 to 1024.

In some cases, the plurality of liquid droplet generators are operable to generate liquid droplets having an individual droplet volume in the range 1 to 100 pL, optionally in the range 5 to 50 pL.

In some cases, the plurality of liquid droplet generators are operable to produce liquid droplets at a frequency in the range 0.1 to 100 kHz, optionally 1 to 10 kHz.

In some cases, the apparatus further comprises a microparticle-receiving means for receiving solid microparticles dispersed in a jet of liquid. In particular, the microparticle-receiving means may comprise a conduit having an opening arranged such that, in use, the jet of second liquid enters said opening downstream of the region of the jet where the liquid droplets enter the jet of second liquid. In some case, the microparticle-receiving means comprises a tube having an opening that faces said nozzle. The tube may be formed of flexible or rigid material and may comprise an elbow bend. Typically, the microparticle-receiving means is able to convert the generally horizontal motion of the microparticle-containing jet into downward vertical motion for collection of the microparticles and/or separation of the microparticles from the second liquid.

In some cases, the microparticle-receiving means comprises a fluid removal means operable to remove fluid from the microparticle-receiving means and a microparticle collection means operable to remove microparticles from the microparticle-receiving means.

In some cases, the apparatus further comprises means for generating a flow of said second liquid through said nozzle. In particular, the means for generating flow may comprise a regulated pressure system for producing a pulseless flow of the liquid. In certain cases, the means for generating flow may comprise a reservoir for holding the second liquid, said reservoir having an outlet in fluid communication with said nozzle.

In some cases, the nozzle has a reduction in cross-sectional area in the direction of flow so as to increase the flow velocity of a liquid passing through the nozzle and thereby form a jet.

In some cases, the apparatus further comprises a camera for monitoring liquid droplets generated by said plurality of liquid droplet generators. Alternatively or additionally, the apparatus may further comprise a light source for illuminating liquid droplets generated by said plurality of liquid droplet generators. In particular, the light source may comprise an LED strobe electrically coordinated with the plurality of liquid droplet generators such that, in use, the camera is able to capture an image of liquid droplets ejected from the plurality of liquid droplet generators at a pre-determined (but typically user-adjustable) time period after ejection of said liquid droplets. For example, the LED strobe may have an adjustable strobe delay, adjustable strobe intensity and/or adjustable pulse width settings, thereby allowing said pre-determined time period after ejection of said droplets to be adjusted.

In some cases, the apparatus further comprises at least one temperature regulator for controlling the temperature of liquid entering said plurality of liquid droplet generators and/or the temperature of liquid entering said nozzle. In particular, the at least one temperature regulator may comprise a first chiller for controlling the temperature of the first liquid entering the plurality of liquid droplet generators in the range of 5° C. to 30° C., optionally in the range 12° C. to 16° C. or 16° C. to 20° C. In certain cases, the at least one temperature regulator comprises a second chiller for controlling the temperature of the second liquid entering the nozzle in the range of 0° C. to 20° C., optionally in the range 2° C. to 8° C. or 3° C. to 9° C.

In some cases, the nozzle is arranged such that, in use, the jet is directed so as to define a horizontal line or arc that passes below the plurality of liquid droplet generators. In particular, the plurality of liquid droplet generators may be arranged such that, in use, the liquid droplets are ejected downwardly with an initial velocity and/or under the assistance of gravity, through said gas, into said jet of second liquid. The plurality of liquid droplet generators may be arranged such that, when viewed from above, the respective outlets of the plurality of liquid droplet generators are in line with and above the jet direction of said nozzle.

In some cases, the outlets of the liquid droplet generators are spaced-apart at equal intervals. In particular, the outlets of adjacent liquid droplet generators may be spaced-apart by between 0.1 and 0.2 mm, measured outlet centre to outlet centre.

In some cases, the plurality of liquid droplet generators are positioned relative to the nozzle such that the distance of travel of a liquid droplet from the outlet of a liquid droplet generator to the nearest point of the jet is in the range 2 to 10 mm, optionally 4 to 6 mm.

In a second aspect, the present invention provides a process for producing solid microparticles, the process comprising:

providing a first liquid comprising a solute and a solvent, the solute comprising a biocompatible polymer, the concentration of polymer in the first liquid being at least 10% w/v, 'w' being the weight of the polymer and 'v' being the volume of the solvent, providing a plurality of liquid droplet generators operable to generate liquid droplets, providing a jet of a second liquid, causing the plurality of liquid droplet generators to form liquid droplets of the first liquid, passing the liquid droplets through a gas to contact the jet of the second liquid so as to cause the solvent to exit the droplets, thus forming solid microparticles, the solubility of the solvent in the second liquid being at least 5 g of solvent per 100 ml of second liquid, the solvent being substantially miscible with the second liquid.

In some cases, the first liquid further comprises at least one (e.g. 1, 2, 3, 4, 5 or more different target materials) target material (also known as a "payload") which is desired to be encapsulated within the microparticles, the target material being incorporated in the first liquid as a particulate or in solution. In certain cases, the target material comprises a pharmaceutically active agent or a precursor of a pharmaceutically active agent. In particular, the target material may be a pharmaceutically active agent for treatment of a tumour, a central nervous system (CNS) condition, an ocular condition, an infection (e.g. viral, bacterial or other pathogen) or an inflammatory condition (including autoinflammatory conditions).

In some cases, the target material may be a peptide, a hormone therapeutic, a chemotherapeutic or an immunosuppressant. In particular, the target material may comprise octreotide or a salt thereof (e.g. octreotide acetate), or ciclosporin A or a salt thereof.

In some cases, the target material may comprise a plurality of nanoparticles. In particular, the nanoparticles may have a pharmaceutically active agent or a precursor of a pharmaceutically active agent covalently or non-covalently (e.g. electrostatically) bound thereto (directly or via one or more linkers). The nanoparticles may, for example, be as described in PCT/EP2015/076364 filed 11 Nov. 2015, published as WO 2016/075211 A1—the entire contents of which is expressly incorporated herein by reference).

In some cases, the plurality of liquid droplet generators comprise at least one piezoelectric component operable to generate droplets.

In particular, the droplet generators may operate in drop-on-demand mode.

In some cases, the respective outlets of the plurality of liquid droplet generators are substantially in line with said jet of second liquid such that the liquid droplets contact the jet of second liquid in parallel spaced along the jet of second liquid.

In some cases, the number of liquid droplet generator outlets is in the range 5 to 2500, such as 100 to 1200, optionally 256, 512 or 1024.

In some cases, the frequency of liquid droplet generation is in the range 0.1 to 100 kHz, optionally 1 to 10 kHz.

In some cases, the liquid droplets have an individual droplet volume in the range 1 to 100 pL, optionally 20 to 60 pL.

In some cases, the mean greatest dimension (typically the diameter) of the solid microparticles is in the range 1 to 200 µm, optionally 10 to 100 µm or 15 to 25 µm or 20 to 40 µm.

In some cases, the coefficient of variation of the greatest dimension of the microparticles is 0.1 or less, the coefficient of variation being the standard deviation of the greatest dimension of the microparticles divided by the mean greatest dimension. The present inventors have found that despite the increased production scale of the method of present invention, the resulting microparticles exhibit excellent uniformity of size and shape, i.e. they form a substantially monodisperse population.

In some cases, the ratio of the greatest dimension to the least dimension of the microparticles is in the range 2 to 1, optionally 1.1 to 1.01. In particular, the microparticles may be substantially spherical ("microspheres").

In some cases, the jet of second liquid is generated by providing a continuous, pulseless flow of said second liquid and passing said flow of second liquid through a nozzle which causes a reduction in the cross-sectional area available for flow and thereby increases the flow velocity of the second liquid, said nozzle terminating in an orifice from which the jet of second liquid emerges.

In some cases, the jet of second liquid passes through a gas (e.g. air).

In some cases, the jet of second liquid is not in contact with any wall or channel for at least part of its length. This differs from prior-described methods, in which the continuous phase is generally provided as a flow in a channel or a pool such as a stirred pool in an open-topped vessel. In particular embodiments, the part of the length of the jet not in contact with any wall or channel comprises a contact zone, said contact zone being the zone of the jet in which said liquid droplets make contact with said jet.

In some cases, the liquid droplets pass through gas (e.g. air) for a distance of 1 to 100 mm, optionally 2 to 10 mm before contacting said jet of second liquid.

In some cases, the jet of second liquid flows substantially perpendicular to the direction of droplet ejection and substantially parallel to the longitudinal axis of the plurality of liquid droplet generator outlets.

In some cases, the plurality of liquid droplet generators are positioned above the jet of second liquid and said liquid droplets are ejected downwards towards the jet of second liquid with an initial velocity and/or under the assistance of gravity.

In some cases, the plurality of liquid droplet generators dispense liquid droplets from their respective outlets simultaneously. In particular, the liquid droplets may pass through gas in parallel before contacting said jet of second liquid.

In some cases, the flow velocity of the jet of second liquid and the frequency of liquid droplet generation are selected such that the liquid droplets and/or the solid microparticles do not coalesce. In particular, the flow rate of the jet of the second liquid may be in the range 10 to 500 mL/min, such as 20 to 200 mL/min or 20 to 100 mL/min.

In some cases, the process is carried out under aseptic conditions, optionally within a laminar flow cabinet. This is particularly suitable when the target material is a pharmaceutical and/or when the microparticles are intended for therapeutic or other clinical use. In the case where the process is carried out in a laminar flow cabinet, the relative position of the plurality of liquid droplet generators and the jet of the second liquid may be chosen to account for the direction and speed of air flow of the laminar flow cabinet, thereby causing the liquid droplets to contact the jet of the second liquid.

In some cases, the process of the invention further comprises capturing one or more images of at least one of said liquid droplets at a pre-determined time point after the at least one liquid droplet has been generated. In particular, the process may further comprise deriving from said one or more images at least one liquid droplet property selected from the group consisting of: droplet velocity, droplet volume, droplet radius and deviation of droplet from its initial trajectory. In this way monitoring (including continuous live monitoring) of droplet properties can be integrated or fed back to adjust, if necessary, one or more process parameters such as droplet generation frequency, the flow rate of the jet of second liquid or the temperature of the first and/or second liquids in order to control the size and other properties of the microparticles produced.

In some cases, the temperature of the first liquid entering the plurality of liquid droplet generators is in the range of 5° C. to 30° C., optionally in the range 12° C. to 16° C. or 16° C. to 20° C.

In some cases, the temperature of the second liquid entering the nozzle is in the range of 0° C. to 20° C., optionally in the range 2° C. to 8° C. or 3° C. to 9° C.

In some cases, the solvent comprises dimethyl sulfoxide (DMSO).

In some cases, the second liquid comprises a mixture of water and an alcohol (e.g. tert-butanol) or water and a water-soluble organic compound other than an alcohol. In particular, the second liquid may be 15% w/w tertiary butanol in water.

In some cases, the polymer comprises a poly(lactide), a poly(glycolide), a polycaprolactone, a polyanhydride and/or a co-polymer of lactic acid and glycolic acid, or is any combination of said polymers or co-polymers. In particular, the polymer may comprise Resomer RG752H, Purasorb PDL 02A, Purasorb PDL 02, Purasorb PDL 04, Purasorb PDL 04A, Purasorb PDL 05, Purasorb PDL 05A Purasorb PDL 20, Purasorb PDL 20A; Purasorb PG 20; Purasorb PDLG 5004, Purasorb PDLG 5002, Purasorb PDLG 7502, Purasorb PDLG 5004A, Purasorb PDLG 5002A, Resomer RG755S, Resomer RG503, Resomer RG502, Resomer RG503H, Resomer RG502H, Resomer RG752, or any combination thereof.

In some cases, the process further comprises collecting the solid microparticles by separating the solid microparticles from the second liquid. In particular, the process may further comprise subjecting the microparticles to one or more post-production treatment steps selected from the group consisting of: washing, heating, drying, freeze-drying and sterilizing.

In some cases, the process further comprises formulating or packaging the microparticles into a pharmaceutical composition or delivery form. For example, the microparticles may be combined with a pharmaceutically acceptable carrier, diluent or vehicle. In some embodiments the pharmaceutical composition or delivery form may be a depot injection.

In some cases, the process of the second aspect of the invention employs an apparatus in accordance with the first aspect of the invention.

In a third aspect, the present invention provides a microparticle produced or producible by the process of the second aspect of the invention.

In a fourth aspect, the present invention provides a pharmaceutical composition comprising a plurality of microparticles of the third aspect of the invention and a pharmaceutically acceptable carrier, diluent, excipient, salt and/or solution.

In a fifth aspect, the present invention provides a liquid stream comprising a plurality of solid polymeric microparticles suspended in the liquid, wherein the flow rate of liquid stream is in the range 0.8 cm$^3$/s to 5 cm$^3$/s and the density of microparticles in the liquid stream is in the range 100000 microparticles/cm$^3$ to 750000 microparticles/cm$^3$. This may be provided, for example, by having a liquid stream with a flow rate of between 50 mL/minute to 300 mL/min and ejecting into the stream liquid droplets at a firing rate of between 1000 Hz and 6000 Hz from each of 512 liquid droplet generator outlets. The liquid droplets solidify by the process of de-solvation (see above) and provide 512000 to 3072000 microparticles/second, which are carried by the flow of the liquid stream. The comparatively high density of microparticles in the flow results in more efficient microparticle production with reduced waste of continuous phase.

The microparticles of the liquid stream of this aspect of the invention may be as defined in connection with the second aspect of the invention. In particular, the microparticles may encapsulate a target material selected from the group consisting of:
   (i) a pharmaceutically active agent or a precursor of a pharmaceutically active agent;
   (ii) a pharmaceutically active agent for treatment of a tumour, a central nervous system (CNS) condition, an ocular condition, an infection or an inflammatory condition;
   (iii) a peptide, a hormone therapeutic, a chemotherapeutic or an immunosuppressant; and
   (iv) a plurality of nanoparticles. Particular examples of target material include: octreotide or a salt thereof (e.g. octreotide acetate) or ciclosporin A or a salt thereof.

In some cases the mean greatest dimension of the solid microparticles is in the range 1 to 200 µm, optionally 10 to 100 µm or 15 to 25 µm or 20 to 40 µm. The coefficient of variation of the greatest dimension of the microparticles may be 0.1 or less, the coefficient of variation being the standard deviation of the greatest dimension of the microparticles divided by the mean greatest dimension. The ratio of the greatest dimension to the least dimension of the microparticles may be in the range 2 to 1, optionally 1.1 to 1.01. The microparticles may be substantially spherical.

In some cases, the liquid stream may be in the form of a jet. The jet may be as defined in connection with the second aspect of the invention. In some cases, the liquid stream of this aspect of the invention may be produced or producible using an apparatus according to the first aspect of the invention.

The present invention includes the combination of the aspects and preferred features described except where such a combination is clearly impermissible or is stated to be expressly avoided. These and further aspects and embodiments of the invention are described in further detail below and with reference to the accompanying examples and figures.

DETAILED DESCRIPTION OF THE INVENTION

Figure 1:
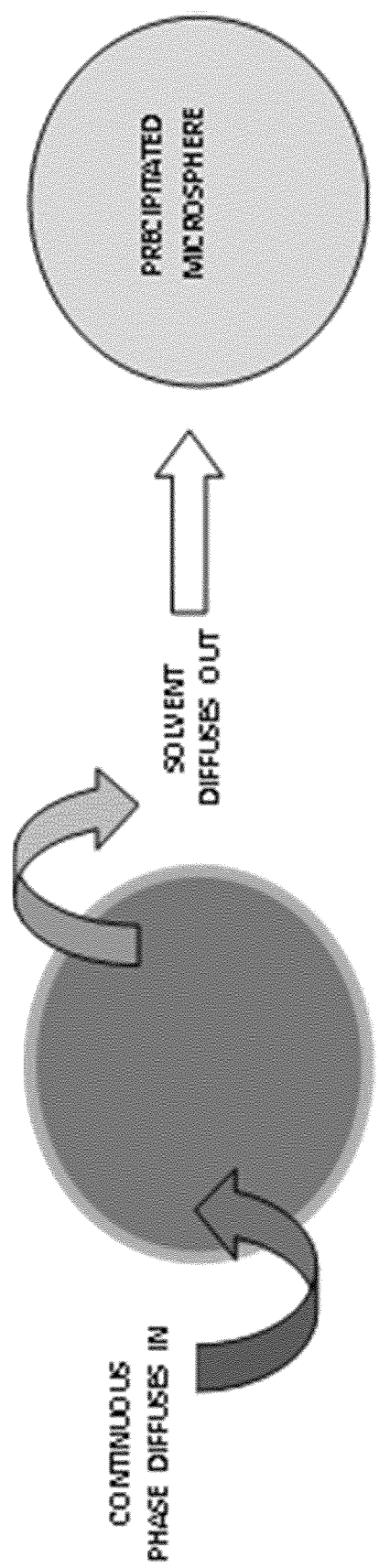
FIG. 1 shows an illustration (not to scale) of the desolvation process by which solvent diffuses out of a liquid droplet in contact with the continuous phase thereby producing a solid microsphere.
Figure 2:
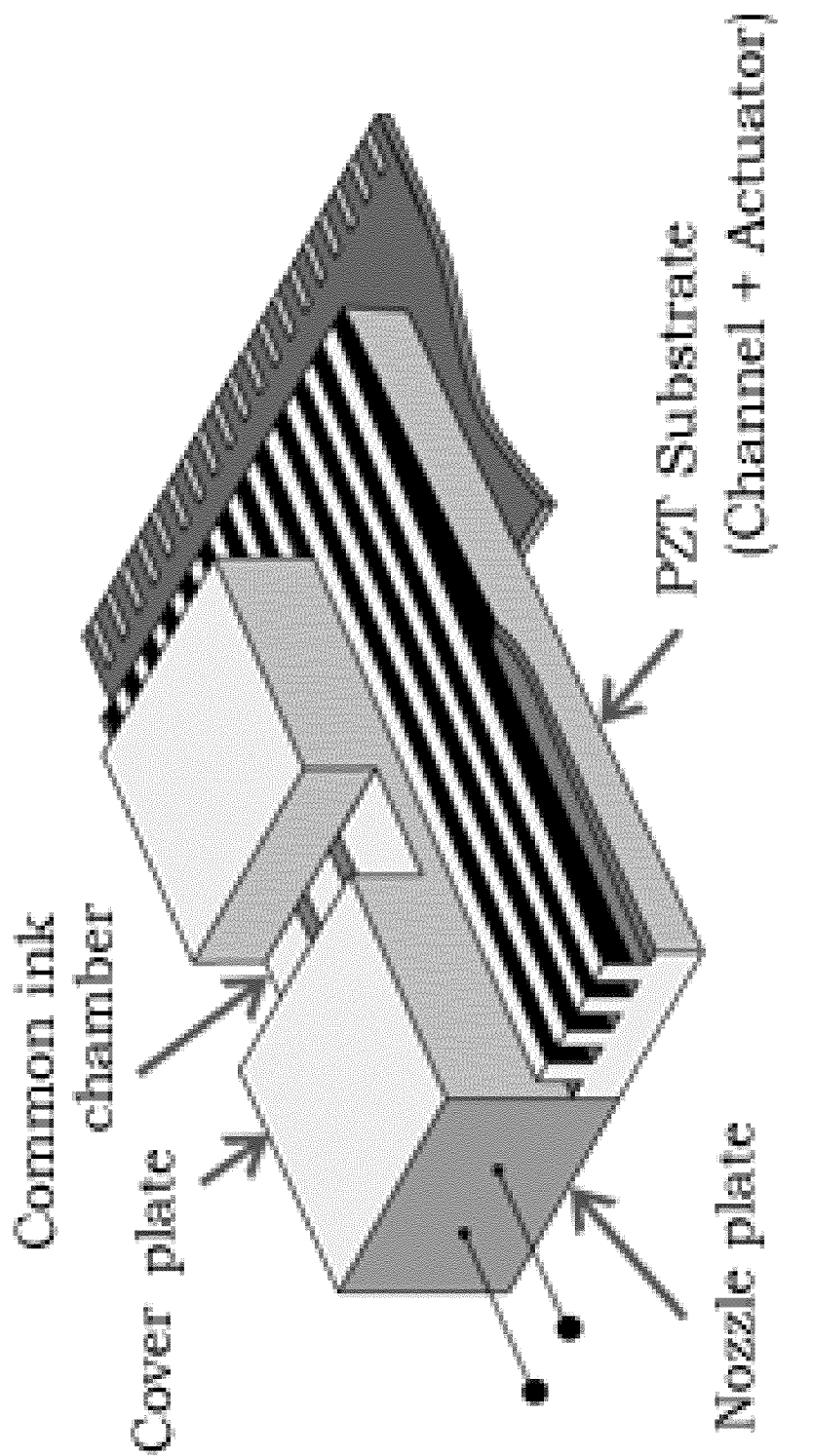
FIG. 2 shows a schematic diagram of a piezoelectric droplet generator (printhead).

In describing the present invention, the following terms will be employed, and are intended to be defined as indicated below.

Microparticles

Microparticles in accordance with the present invention may be in the form of solid beads. As used herein in connection with microparticles or beads, solid is intended to encompass a gel. Microparticles as used herein specifically include any polymeric particle or bead of micron scale (typically from 1 µm up to 999 µm in diameter). The microparticles may be of substantially spherical geometry (also referred to herein as "microspheres"). In particular, the ratio of the longest dimension to the shortest dimension of the microparticle may be not more than 5, 4, 3, 2, 1.9, 1.8, 1.7, 1.6, 1.5, 1.4, 1.3, 1.2, 1.1, 1.05 or not more than 1.01.

Jet

As used herein, a "jet" is a coherent stream of fluid that is projected into a surrounding medium from a nozzle or aperture. In particular, a jet of second liquid (continuous phase) may be a coherent stream of the second liquid projected into a gas (typically air) from a nozzle. The jet may define a flow path, at least part of which is not in contact with any solid wall, conduit or channel. The jet may define a flow path (e.g. a line or arc) that intersects with the path or paths of liquid droplets dispensed from the plurality of droplet generators. For example, the jet may be a stream of the second liquid passing through air below the plurality of droplet generators, whereby liquid droplets dispensed from the droplet generators pass through the gas under the assistance of gravity into the stream of the second liquid and are carried by said stream of second liquid. Typically, surface tension of the second liquid contributes to the jet taking the form of coherent stream. In some cases, the jet has a substantially circular cross-section. However, other cross sectional shapes (e.g. flattened or oval-like) are specifically contemplated and may be provided, e.g., by means of particular nozzle shapes.

Biocompatible Polymer

The polymer is typically a biocompatible polymer. "Biocompatible" is typically taken to mean compatible with living cells, tissues, organs, or systems, and posing minimal or no risk of injury, toxicity, or rejection by the immune system. Examples of polymers which may be used are polylactides (with a variety of end groups), such as Purasorb PDL 02A, Purasorb PDL 02, Purasorb PDL 04, Purasorb PDL 04A, Purasorb PDL 05, Purasorb PDL 05A Purasorb PDL 20, Purasorb PDL 20A; polyglycolides (with a variety of end groups), such as Purasorb PG 20; polycaprolactones; polyanhydrides, and copolymers of lactic acid and glycolic acid (with a variety of end groups, L:G ratios and molecular weight can be included), such as Purasorb PDLG 5004, Purasorb PDLG 5002, Purasorb PDLG 7502, Purasorb PDLG 5004A, Purasorb PDLG 5002A, resomer RG755S, Resomer RG503, Resomer RG502, Resomer RG503H, Resomer RG502H, RG752, RG752H, or combinations thereof. In some cases, it is preferred that the solute is substantially insoluble in water (it is convenient to use water as the second liquid). If the second liquid comprises water, it is preferred that the solvent is a water-miscible organic solvent, such as dimethyl sulfoxide (DMSO), n-methyl pyrrolidone, hexafluoro-isopropanol, glycofurol, PEG200 and PEG400.

The weight average molecular weight (MW) of the polymer may be from 4 to 700 kDaltons, particularly if the polymer comprises a poly (α-hydroxy) acid. If the polymer comprises a copolymer of lactic and glycolic acid (often called "PLGA"), said polymer may have a weight average molecular weight of from 4 to 120 kDaltons, preferably of from 4 to 15 kDaltons.

If the polymer comprises a polylactide, said polymer may have a weight average molecular weight of from 4 to 700 kDaltons.

The polymer may have an inherent viscosity of from 0.1-2 dl/g, particularly if the polymer comprises a poly (α-hydroxy) acid. If the polymer comprises a copolymer of lactic and glycolic acid (often called "PLGA"), said polymer may have. an inherent viscosity of from 0.1 to 1 dl/g, and optionally of from 0.14 to 0.22 dl/g. If the polymer comprises a polylactide, said polymer may have an inherent viscosity of from 0.1 to 2 dl/g, and optionally of from 0.15 to 0.25 dl/g. If the polymer comprises a polyglycolide, said polymer may have an inherent viscosity of from 0.1 to 2 dl/g, and optionally of from 1.0 to 1.6 dl/g. It is preferred that the first liquid comprises a target material which is desired to be encapsulated within the solid microparticles. However, it is specifically contemplated herein that the process of the present invention may, in certain cases, not include a target material. For example, the process may be used to produce placebo microparticles, e.g., for use as a negative control in an experiment or clinical trial.

Target Material

The target material (also known as the "payload") may be incorporated in the first liquid as a particulate or may be dissolved. The target material may comprise a pharmaceutically active agent, or may be a precursor of a pharmaceutically active agent. In some cases, the target material comprises a pharmaceutically active agent, or precursor (e.g. prodrug) thereof, for treatment of a tumour, a central nervous system (CNS) condition, an ocular condition, an infection or an inflammatory condition. In some cases, the target material may comprise a peptide, a hormone therapeutic, a chemotherapeutic or an immunosuppressant. In certain cases, said target material comprises a plurality of nanoparticles (e.g. gold nanoparticles). When present, such nanoparticles may have a pharmaceutically active agent or a precursor thereof covalently or non-covalently bound thereto.

Examples of pharmaceutically active agent include, for example, any agent that is suitable for parenteral delivery, including, without limitation, fertility drugs, hormone therapeutics, protein therapeutics, anti-infectives, antibiotics, antifungals, cancer drugs, pain-killers, vaccines, CNS drugs, and immunosupressants. Particular examples include octreotide or salt thereof (e.g. octreotide acetate) and ciclosporin A or a salt thereof.

The delivery of drugs in polymer microparticles, especially by controlled release parenteral, intravitreal or intracranial delivery, has particular advantages in the case of drugs which, for example, have poor water-solubility, high toxicity, poor absorption characteristics, although the invention is not limited to use with such agents. The active agent may be, for example, a small molecular drug, or a more complex molecule such as a polymeric molecule. The pharmaceutically active agent may comprise a peptide agent. The term "peptide agent" includes poly(amino acids), often referred to generally as "peptides", "oligopeptides", "polypeptides" and "proteins". The term also includes peptide agent analogues, derivatives, acylated derivatives, glycosylated derivatives, pegylated derivatives, fusion proteins and the like. Peptide agents which may be used in the method of the present invention include (but are not limited to) enzymes, cytokines, antibodies, vaccines, growth hormones and growth factors.

The target material (especially in the case of a pharmaceutically active agent or a precursor thereof) may be provided in an amount of 2-60% w/w compared to the weight of the polymer, optionally from 5 to 40% w/w, further optionally from 5 to 30% w/w and more optionally from 5-15% w/w.

If the target material comprises a peptide agent, the first liquid may comprise one or more tertiary structure alteration inhibitors. Examples of tertiary structure alteration inhibitors are: saccharides, compounds comprising saccharide moieties, polyols (such as glycol, mannitol, lactitol and sorbitol), solid or dissolved buffering agents (such as calcium carbonate and magnesium carbonate) and metal salts (such as $CaCl_2$, $MnCl_2$, NaCl and $NiCl_2$). The first liquid may comprise up to 25% w/w tertiary structure alteration inhibitors, the weight percentage of the tertiary structure alteration inhibitor being calculated as a percentage of the weight of the polymer. For example, the first liquid may comprise from 0.1 to 10% w/w (optionally from 1 to 8% w/w and further optionally from 3 to 7% w/w) metal salt and 0.1 to 15% w/w (optionally from 0.5 to 6% w/w and further optionally from 1 to 4% w/w) polyol.

Second Liquid

The second liquid (also referred to herein as the "continuous phase") may comprise any liquid in which the solute (typically a polymer) is substantially insoluble. Such a liquid is sometimes referred to as an "anti-solvent". Suitable liquids may include, for example, water, methanol, ethanol, propanol (e.g. 1-propanol, 2-propanol), butanol (e.g. 1-butanol, 2-butanol or tert-butanol), pentanol, hexanol, heptanol, octanol and higher alcohols; diethyl ether, methyl tert butyl ether, dimethyl ether, dibutyl ether, simple hydrocarbons, including pentane, cyclopentane, hexane, cyclohexane, heptane, cycloheptane, octane, cyclooctane and higher hydrocarbons. If desired, a mixture of liquids may be used.

The second liquid preferably comprises water, optionally with one or more surface active agents, for example, alcohols, such as methanol, ethanol, propanol (e.g. 1-propanol, 2-propanol), butanol (e.g. 1-butanol, 2-butanol or tert-butanol), isopropyl alcohol, Polysorbate 20, Polysorbate 40, Polysorbate 60 and Polysorbate 80. Surface active agents, such as alcohols, reduce the surface tension of the second liquid receiving the droplets, which reduces the deformation of the droplets when they impact the second liquid,—thus decreasing the likelihood of non-spherical droplets forming. This is particularly important when the extraction of solvent from the droplet is rapid. If the second liquid comprises water and one or more surface active agents, the second liquid may comprise a surface active agent content of from 1 to 95% v/v, optionally from 1 to 30% v/v, optionally from 1 to 25% v/v, further optionally from 5% to 20% v/v and further more optionally from 10 to 20% v/v. The % volume of surface active agent is calculated relative to the volume of the second liquid.

Printhead

As used herein, "printhead" or "inkjet printhead" may be a component, typically employed in inkjet printing or inkjet material deposition, which comprises one or more chambers that act as reservoirs for a fluid to be ejected and at least two nozzles through which droplets of the fluid are ejected by virtue of force applied by a piezoelectric material operating in drop-on-demand mode. The nozzles of the inkjet printhead may be arranged in a regular pattern, such as a single row or an array having more than one row. The inkjet printhead may be a commercially available "off the shelf" inkjet printhead used "as is" or may be adapted for use in the microparticle generating methods of the present invention or may be custom made for use in the microparticle generating methods of the present invention. An example of a printhead for use in accordance with the present invention is the Konica Minolta 512LH print head, e.g. KM512LH-010532.

The entire contents of WO2012/042274, WO 2012/042273 and WO 2013/014466 are expressly incorporated herein by reference for all purposes.

The following is presented by way of example and is not to be construed as a limitation to the scope of the claims.

EXAMPLE

Example 1

Microsphere Generation

The present invention aims to provide consistent and precise encapsulation of active drug compounds within polymer microspheres designed to release the drug into the body in a controlled manner over a prolonged period of time.

The present example employs drop-on-demand inkjet technology to produce droplets in the picolitre (pL) range. The technology has been proven to produce discrete, repeatable droplets at frequencies of several kHz across multiple nozzles. Optimisation of the pressure pulse is achieved by adjusting the magnitude and duration of the electrical field supplied. The temperature at the nozzle plate can also be controlled in order to alter the viscosity of the fluid at the point of ejection.

Droplet formation is tracked using an advanced viewing system ("JetXpert") supplied by ImageXpert. The system includes a camera and LED strobe which is triggered each time a firing signal (5 Volt P-P Square Wave 50% duty cycle) is sent to the actuator of the droplet generator. The result is a static, monochromatic image of the ejected droplet at a pre-determined time period after ejection, which is refreshed over a pre-determined time allowing for monitoring of droplets potentially falling out of specification. This time period is known as the strobe delay and can be input to the software by a process operator. The delay is variable, and hence the entire droplet formation period is traceable. The system allows for viewing droplets "in motion" by assigning a Start value, End value and Step size via nanoseconds which in turn automatically starts increasing the strobe delay to follow the droplet formation and ejection path until the pre-set termination point.

The viewing system can be calibrated to allow the user to ascertain important properties of the ejected droplets; namely velocity (metres per second), volume (pL), radius (μm) and its deviation from its original trajectory (values are provided via mean, standard deviation, minimum and maximum). These data can be automatically recorded in a spreadsheet to act as a batch record. Images and videos may also be taken when data is not being recorded The second fluid passes across the underside of the generator. The droplets are ejected into air, initially, before being captured by the horizontal cross flow of fluid (i.e. the jet), collecting all droplets from all nozzles in one stream.

Figure 3:
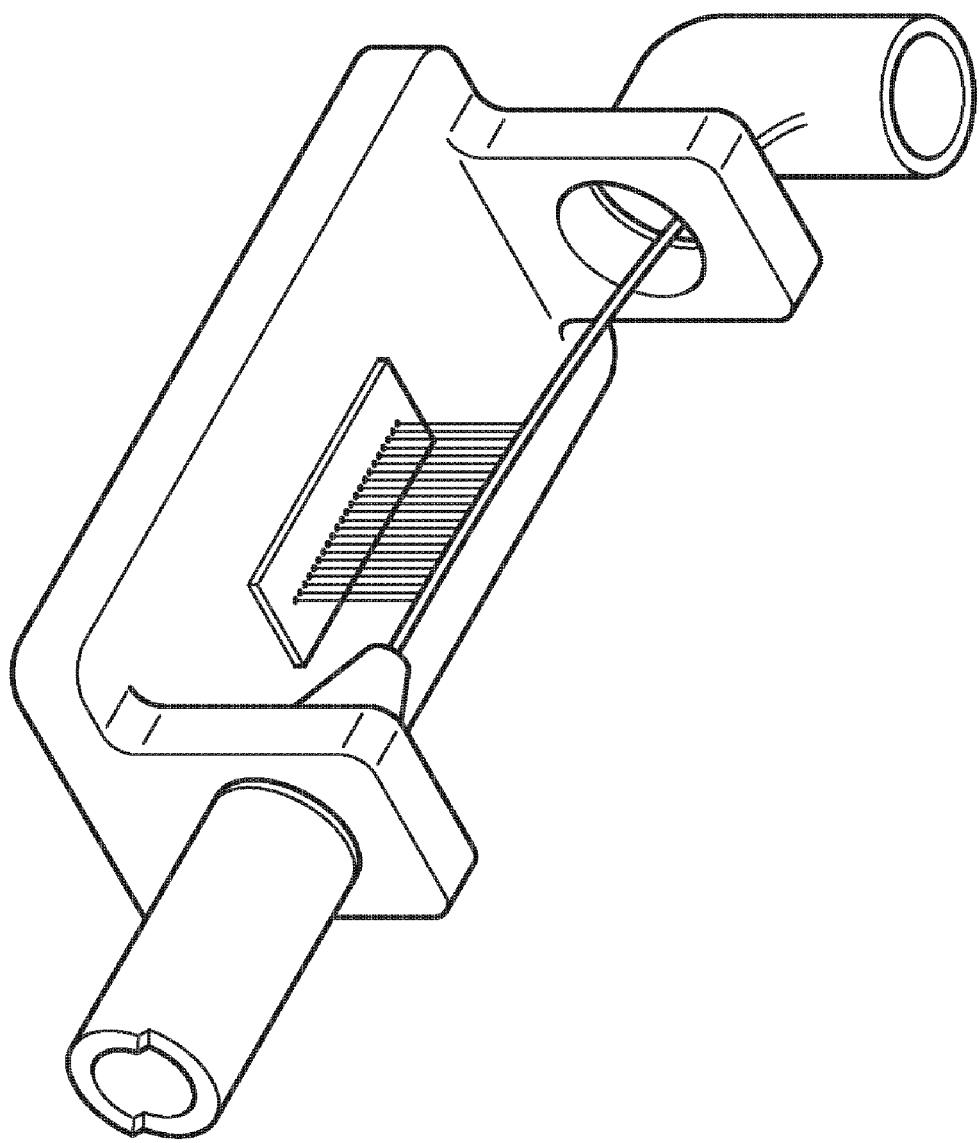
FIG. 3 shows a schematic illustration of an apparatus embodiment of the invention.

The flow beneath the droplet generator is laminar (i.e. the jet of second liquid defines a generally horizontal line or arc that passes under the droplet generator), as seen in FIG. 3. The present inventors have designed a nozzle containing an abrupt reduction to the circular cross-sectional area available for flow. This serves to increase the flow velocity in the region immediately below the generator, with the aim of ensuring ejected droplets do not coalesce. The velocity of the jet is such that droplets are immediately removed from the path of those behind them. Continuous, pulseless flow is provided by a regulated pressure system.

Logic would suggest that the optimal way of avoiding coalescence would be to provide a wide flow channel at 90° to the generator's nozzle plate. However, through experimentation, the present inventors have found that precipitation is virtually instant and that firing directly along the line of the nozzle plate leads to a significant reduction in the consumption of the continuous phase, which in turn reduces cost and waste from the process.

The continuous phase nozzle is mounted on a bespoke bracket designed by the present inventors which attaches to the a custom aspect-ready framework to which is in turn attached the JetXpert peripherals. Directly opposite the nozzle on the other side of the droplet generator is a receiving elbow to capture the stream which now contains solidified spheres.

Both process fluids' temperatures are controlled by programmable chilling systems. The anti-solvent is chilled in-line upstream of the anti-solvent nozzle. At their point of contact, the continuous phase is 3-9° C. The dispersed phase is held at approximately 16° C. in order to maintain the stability of the drug-loaded formulation, but also to avoid freezing when agitated through priming and vacuum changes.

The above-described method of microparticle generation was found to produce a larger number of microparticles per unit time and a relatively lower volume of anti-solvent was required per microparticle produced when compared with the single droplet generator nozzle per channel method described in WO2012/042273 and WO2012/042274. For example, when an inkjet printhead having 512 liquid droplet generator outlets is employed with a firing rate of 2000 to 6000 Hz, the number of microparticles produced is in the range 1024000 to 3072000 microparticles per second. The above-described method therefore provides greater potential for industrial-scale production and increased efficiency. The liquid stream containing the formed solid microparticles has a greater density of microparticles such that there is lower level of waste of the continuous phase for a given quantity of microparticles produced. Nevertheless, the microparticles produced were found to exhibit excellent uniformity, i.e. they were highly monodisperse.

Example 2

Octreotide-Loaded Microparticles

A particular example of the process of microparticle production described above in Example 1 is the production of octreotide-loaded microspheres (Q-Octreotidem) now described.

Octreotide (also known by the brand name Sandostatin®, Novartis Pharmaceuticals) is an octapeptide that mimics somatostatin pharmacologically. Octreotide has the following chemical structure:

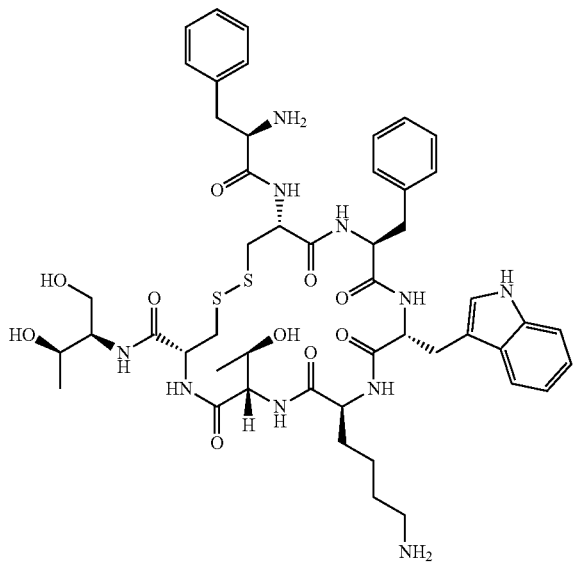 [SMILES: C[C@@H](O)[C@@H]1NC(=O)[C@H](CCCCN)NC(=O)[C@@H](Cc2c[nH]c3ccccc23)NC(=O)[C@H](Cc2ccccc2)NC(=O)[C@@H](NC(=O)[C@H](N)Cc2ccccc2)CSSC[C@@H](C(=O)N[C@H](CO)[C@@H](C)O)NC1=O]

Octreotide is used for the treatment of growth hormone producing tumours (acromegaly and gigantism), pituitary tumours that secrete thyroid stimulating hormone (thyrotropinoma), diarrhoea and flushing episodes associated with carcinoid syndrome, and diarrhoea in people with vasoactive intestinal peptide-secreting tumours (VIPomas).

Materials

| Material | Use | Supplier |
|---|---|---|
| Anhydrous DMSO | Solvent for PLGA and octreotide acetate | Sigma |
| Resomer RG752H | Rate controlling excipient Poly(D,L-lactide-co-glycolide) acid terminated, lactide:glycolide 75:25 | Evonik |
| Octreotide acetate | Active | PolyPeptide Inc |
| Ultrapure water | Equipment rinsing, antisolvent, wash solutions, lyophilisation media | Lab water system |
| Tert-Butanol | Antisolvent | VWR |
| D-Mannitol | Wash media and freeze dry excipient | Sigma |
| PBS | Wash media | Sigma |
| CMC | Freeze dry excipient | Sigma |
| Tween20 | Freeze dry excipient | Sigma |

| Equipment | Comments |
|---|---|
| PiezoArray Printhead | Konica Minolta KM512LH-010532 printhead, new, cleaned as for leachables and extractables. Pre-flushed with DMSO prior to batch start |

Methodology

A master formulation is made up:

Resomer RG752H

Octreotide acetate

DMSO

The active solution is maintained at 12-16° C.

Antisolvent

15% w/w tertiary butanol.

Dispensing Droplets

KM512LH head was run with frequency set to 4 kHz.

Antisolvent Flow 125 mL/min, 2-8° C.

The octreotide-loaded microspheres were collected using a bead harvester (see WO2013/014466), washed, freeze-dried and terminally sterilized (e.g. using gamma ray or E-beam sterilization).

The octreotide-loaded microspheres were determined to be monodisperse and suitable for sustained release pharmaceutical use.

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Any sub-titles herein are included for convenience only, and are not to be construed as limiting the disclosure in any way.

The invention claimed is:

1. A process for producing solid microparticles, the process comprising:
providing a first liquid comprising a solute and a solvent, the solute comprising a biocompatible polymer, the concentration of polymer in the first liquid being at least 10% w/v, 'w' being the weight of the polymer in g and 'v' being the volume of the solvent in mL,
providing a plurality of liquid droplet generators operable to generate liquid droplets, wherein the plurality of liquid droplet generators comprise at least one piezoelectric component operable to generate droplets and wherein the plurality of liquid droplet generators are operable to produce liquid droplets at a frequency in the range 1 to 100 kHz per droplet generator,
providing a jet of a second liquid,
causing the plurality of liquid droplet generators to form liquid droplets of the first liquid,
passing the liquid droplets through a gas to contact the jet of the second liquid in a contact zone of said jet of the second liquid so as to cause the solvent to exit the droplets, thus forming solid microparticles,
the solubility of the solvent in the second liquid being at least 5 g of solvent per 100 ml of second liquid, the solvent being substantially miscible with the second liquid, and
wherein the jet of the second liquid is not in contact with any wall or channel for at least the length of said contact zone.

2. The process according to claim 1, wherein the first liquid further comprises a target material which is desired to be encapsulated within the microparticles, the target material being incorporated in the first liquid as a particulate or in solution.

3. The process according to claim 2, wherein said target material comprises a pharmaceutically active agent or a precursor of a pharmaceutically active agent.

4. The process according to claim 3, wherein said target material comprises a pharmaceutically active agent for treatment of a tumour, a central nervous system (CNS) condition, an ocular condition, an infection or an inflammatory condition.

5. The process according to claim 3, wherein said target material comprises a peptide, a hormone therapeutic, a chemotherapeutic or an immunosuppressant.

6. The process according to claim 5, wherein said target material comprises octreotide or a salt thereof, or ciclosporin A or a salt thereof.

7. The process according to claim 1, wherein the respective outlets of the plurality of liquid droplet generators are substantially in line with said jet of second liquid such that the liquid droplets contact the jet of second liquid in parallel spaced along the jet of second liquid.

8. The process according to claim 7, wherein said jet of second liquid flows substantially perpendicular to the direction of droplet ejection.

9. The process according to claim 1, wherein the number of liquid droplet generator outlets is in the range 5 to 2500.

10. The process according to claim 1, wherein said liquid droplets have an individual droplet volume in the range 1 to 100 pL.

11. The process according to claim 1, wherein the mean greatest dimension of the solid microparticles is in the range 1 to 200 μm.

12. The process according to claim 1, wherein the microparticles are substantially spherical.

13. The process according to claim 1, further comprising capturing one or more images of at least one of said liquid droplets at a pre-determined time point after the at least one liquid droplet has been generated, and further comprising deriving from said one or more images at least one liquid droplet property selected from the group consisting of: droplet velocity, droplet volume, droplet radius, and deviation of droplet from its initial trajectory.

14. The process according to claim 1, wherein the temperature of the first liquid entering the plurality of liquid droplet generators is in the range of 5° C. to 30° C.; and/or wherein the temperature of the second liquid entering the nozzle is in the range of 0° C. to 20° C.

15. The process according to claim 1, wherein the polymer comprises a poly(lactide), a poly(glycolide), a polycaprolactone, a polyanhydride and/or a co-polymer of lactic acid and glycolic acid or is any combination of said polymers or co-polymers.

16. The process according to claim 1, wherein the process further comprises collecting the solid microparticles by separating the solid microparticles from the second liquid.

17. The process according to claim 16, wherein the process further comprises subjecting the microparticles to one or more post production treatment steps selected from the group consisting of: washing, heating, drying, freeze-drying and sterilizing.

18. The process according to claim 17, wherein said post-production treatment step comprises heating.

19. The process according to claim 16, wherein the process further comprises formulating or packaging the microparticles into a pharmaceutical composition or delivery form.

20. The process according to claim 1, wherein the process employs an apparatus comprising:

a plurality of liquid droplet generators for forming liquid droplets of a first liquid, wherein the plurality of liquid droplet generators comprise at least one piezoelectric component operable to generate droplets; and a nozzle for forming a jet of a second liquid, wherein the plurality of liquid droplet generators and the nozzle are arranged relative to each other such that, in use, liquid droplets from the plurality of liquid droplet generators pass through a gas into said jet of second liquid, and wherein, in use, the plurality of liquid droplet generators are operable to produce liquid droplets at a frequency in the range 1 to 100 kHz per droplet generator.

* * * * *